US006301497B1

(12) United States Patent
Neustadter (10) Patent No.: US 6,301,497 B1
(45) Date of Patent: *Oct. 9, 2001

(54) METHOD AND APPARATUS FOR MAGNETIC RESONANCE IMAGING INTERSECTING SLICES

(75) Inventor: David Maier Neustadter, D.N. Sharon Tichon (IL)

(73) Assignee: GE Medical Systems Global Technology Company, LLC, Waukesha, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/351,495

(22) Filed: Jul. 12, 1999

(51) Int. Cl.⁷ ............................................ A61B 5/055
(52) U.S. Cl. ..................... 600/410; 324/309; 128/920
(58) Field of Search ......................... 600/407, 410; 324/309; 128/920, 922; 382/128

(56) References Cited

U.S. PATENT DOCUMENTS

| 5,512,826 | * | 4/1996 | Hardy et al. . |
| 5,512,827 | * | 4/1996 | Hardy et al. . |
| 5,545,992 | * | 8/1996 | Foo . |
| 5,613,492 | * | 3/1997 | Feinberg . |
| 5,749,834 | * | 5/1998 | Hushek . |
| 5,891,030 | * | 4/1999 | Johnson et al. . |
| 6,108,573 | * | 8/2000 | Debbins et al. . |

OTHER PUBLICATIONS

Hardy, Christopher J. et al. Interactive Coronary MRI. MRM 40:106–111 (1998), pp. 105–111.

David M. Kramer et al., *Fluoroscopic MR Imaging at 0.064 Tesla*, IEEE Transactions On Medical Imaging, vol. 10, No. 3, Sep. 1991, pp. 358–361, Institute of Electrical and Electronics Engineers, New York, NY.

\* cited by examiner

Primary Examiner—Marvin M. Lateef
Assistant Examiner—Shawna J Shaw
(74) Attorney, Agent, or Firm—Foley & Lardner (57) ABSTRACT

A method and apparatus capable of interactively identifying and tracking the movement and orientation of a freely moving structure of interest is disclosed herein. The MR imaging system includes an operator interface for displaying three MR images that are oriented to and with each other in any pre-determined orientation including an intersecting orthogonal orientation and an intersecting radial orientation. The three MR images are continuously updated in real-time and acquired interleaved. The MR imaging system further includes interactive controls to prescribe a scan plane of at least one of the subsequent three MR images, to store at least one of the MR image, and to retrieve at least one of the stored MR image.

98 Claims, 3 Drawing Sheets

METHOD AND APPARATUS FOR MAGNETIC RESONANCE IMAGING INTERSECTING SLICES

BACKGROUND OF THE INVENTION

The present invention relates generally to magnetic resonance (MR) imaging systems and methods. More particularly, the present invention relates to a MR imaging system equipped for real-time imaging and which permits an operator to identify and track movement of a freely moving structure of interest positioned therein.

When an object such as human tissue is subjected to an uniform magnetic field (polarizing field $B_0$, referred to as the z direction in x, y, z coordinates), the individual magnetic moments of the spins in the tissue attempt to align with this polarizing field, but precess about it at their characteristic Larmor frequency. If the object, or tissue, is subjected to a magnetic field (excitation field $B_1$) which is in the x-y plane and which is near the Larmor frequency, the net aligned moment, $M_z$, may be rotated, or "tipped" at a certain tipping angle, into the x-y plane to produce a net traverse magnetic moment M. A signal is emitted by the excited spins after the excitation signal $B_1$ is terminated and this signal may be received and processed to form a MR image.

When utilizing these signals to produce images, magnetic field gradients ($G_x$, $G_y$, and $G_z$) are employed. Typically, the object, or tissue, to be imaged is scanned by a sequence of measurement cycles in which these gradients vary according to the particular localization method being used. The resulting set of received nuclear magnetic resonance (NMR) signals, also referred to as MR signals, are digitized and processed to reconstruct the image using one of many well-known reconstruction techniques.

Presently, when imaging a static or quasi-static object such as the heart, because its movements are predictable or minimal, it is possible to observe the movement and identify the orientation of the object through a series of single images. Each image would be adequately presented by providing the scanning or imaging plane orientation relative to a fixed reference frame in the MR imaging system, or preferably, relative to the object itself. This scheme also works well for objects having gross bulk movements as long as the movements are known and predictable, such as in kinematic joint studies.

In contrast, with a freely moving object such as a fetus, it is often difficult to identify and track the movement and orientation of such an object from a series of single images. In fact, because the object's movements are unpredictable as well as possibly being gross bulk movements, the operator is essentially chasing and trying to keep up with the freely moving object throughout the series of images. Thus, the scanning and viewing protocol presently used for static or quasi-static objects are not well-suited for freely moving objects. First, from the resulting changes in a single image (from the preceding images), movement of a freely moving object is difficult to identify. Specifically, movement of the object in the plane of the image is readily ascertainable, but movement perpendicular to the plane of the image or out-of-plane rotations are not easy to identify from a single image.

Second, providing the imaging plane orientation of each image relative to a fixed reference frame is not useful for a freely moving object because the operator still has no information as to the orientation of the object relative to that fixed reference frame. In other words, when a patient lies down in the MR imaging system and stays in one orientation, the orientation of the patient relative to the system is known. This enables the system to present the orientation of the imaging plane with respect to the patient which is sufficient to orient the operator on what he or she is viewing. In this way, even images that are highly symmetrical, such as axial slices through the brain, have their orientation clearly identified. However, when the object is a fetus, for example, providing orientation of the imaging plane relative to the mother gives no information as to the orientation of the freely moving fetus itself. Therefore, the common practice of providing orientation information based on a fixed reference frame is insufficient when imaging freely moving objects.

Third, in many MR imaging systems, the quickest and easiest way to prescribe the desired imaging plane is by specifying a line on a scout image through which the subsequent imaging plane of the subsequent image will intersect perpendicularly. However, because these scout images are typically not updated continuously in real-time, imaging plane prescription using a scout image for a freely moving object would always be outdated and consequently result in a subsequent image which bears little resemblance to the desired image.

Thus, there is a need for a MR imaging system having one or more of the following features: the capability to image static, quasi-static, and freely moving objects; provide an improved object movement identification scheme, an improved object orientation identification scheme, and an improved imaging plane prescription scheme; provide improved archival of images such that desired images may be easily retrieved based on specific retrieval criteria; and provide improved performance parameters described above without unduly lengthening the acquisition, reconstruction, or display time of images, requiring extensive additional system components, requiring extensive operator training, nor causing significant degradation in existing image quality.

BRIEF SUMMARY OF THE INVENTION

One embodiment of the invention relates to a method for viewing of a structure of interest positioned in a magnetic resonance (MR) imaging system. The method includes generating a main MR image, configuring a main MR imaging pulse sequence of the main MR image to cause a main tip angle, and displaying the main MR image. The method further includes generating a first intersecting MR image, configuring a first intersecting MR imaging pulse sequence of the first intersecting MR image to cause a first intersecting tip angle, and displaying the first intersecting MR image. The method still further includes generating a second intersecting MR image, configuring a second intersecting MR imaging pulse sequence to cause a second intersecting tip angle, and displaying the second intersecting MR image. At least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

Another embodiment of the invention relates to a system for viewing of a structure of interest positioned therein. The system includes means for generating a main MR image, a first intersecting MR image, and a second intersecting MR image. The system further includes means for configuring a main MR imaging pulse sequence to cause a main tip angle, a first intersecting MR imaging pulse sequence to cause a first intersecting tip angle, and a second intersecting MR imaging pulse sequence to cause a second intersecting tip angle. The system still further includes means for displaying the main, first intersecting, and second intersecting MR images. At least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

Another embodiment of the invention relates to a MR imaging system including a MR imaging device configured to generate a main, a first intersecting, and a second intersecting MR image, and configured to cause a main, a first intersecting, and a second intersecting tip angle, respectively. The system further includes an operator interface coupled tot he MR imaging device, configured to display the main, first intersecting, and second intersecting MR images. At least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

Another embodiment of the invention relates to a method for generating and displaying a main MR image, a first intersecting MR image, and a second intersecting MR image. The method further includes the generating and displaying of above a plurality of times as desired in continuous real-time. The generation of the first and second intersecting MR images alternates and thereinbetween, interleaved with the generation of the main MR image.

Another embodiment of the invention relates to a MR imaging system including means for generating and displaying a main MR image, a first intersecting MR image, and a second intersecting MR image. The system further includes means for generating and displaying of above a plurality of times as desired in continuous real-time. The generation of the first and second intersecting MR images alternates and thereinbetween, interleaved with the generation of the main MR image.

Another embodiment of the invention relates to a MR imaging system including a MR imaging device configured to generate a main, a first intersecting, and a second intersecting MR image. The system further includes an operator interface coupled to the MR imaging device, configured to display the main, first intersecting, and second intersecting MR images. The main, first intersecting, and second intersecting MR images are updated continuously in real-time as desired, the generation of the first and second intersecting MR images alternating and thereinbetween interleaved with the generation of each of the main MR image.

Another embodiment of the invention relates to a method of generating and displaying a main, a first intersecting, and a second intersecting MR image. The method further includes selectively storing at least one of the main, first intersecting, and second intersecting MR image, its associated unique identification scheme, and optionally its unique image name label. The method further includes selectively retrieving at least one of the main, first intersecting, and second intersecting MR image stored based on at least one criterion of the unique identification scheme.

Another embodiment of the invention relates to a graphical user interface including a means for displaying a main, a first intersecting, and a second intersecting MR image. The graphical user interface further includes a means for selectively storing at least one of the main, first intersecting, and second intersecting MR image, its associated unique identification scheme, and optionally a unique image name label in the MR imaging system. The graphical user interface further includes a means for selectively retrieving at least one of the main, first intersecting, and second intersecting MR image stored in the MR imaging system based on at least one criterion of the unique identification scheme.

Still anther embodiment of the invention related to a MR imaging system including a MR imaging device configured to generate a main, a first intersecting, and a second intersecting MR image. The system further includes an operator interface coupled to the MR imaging device, configured to display the main, first intersecting, and second intersecting MR images. The system still further includes a storage device coupled to the MR imaging device and configured to selectively store at least one of the main, first intersecting, and second intersecting MR image, its associated unique identification scheme, and optionally a unique image name label. The storage device is further configured to selectively retrieve at least one of the main, first intersecting, and second intersecting MR image stored therein, the retrieval based on at least one criterion of the unique identification scheme.

BRIEF DESCRIPTION OF THE DRAWINGS

One embodiment of the present invention will become more fully understood from the following detailed description, taken in conjunction with the accompanying drawings, wherein like reference numerals refer to like parts, in which.

DETAILED DESCRIPTION OF THE INVENTION

Figure 1:
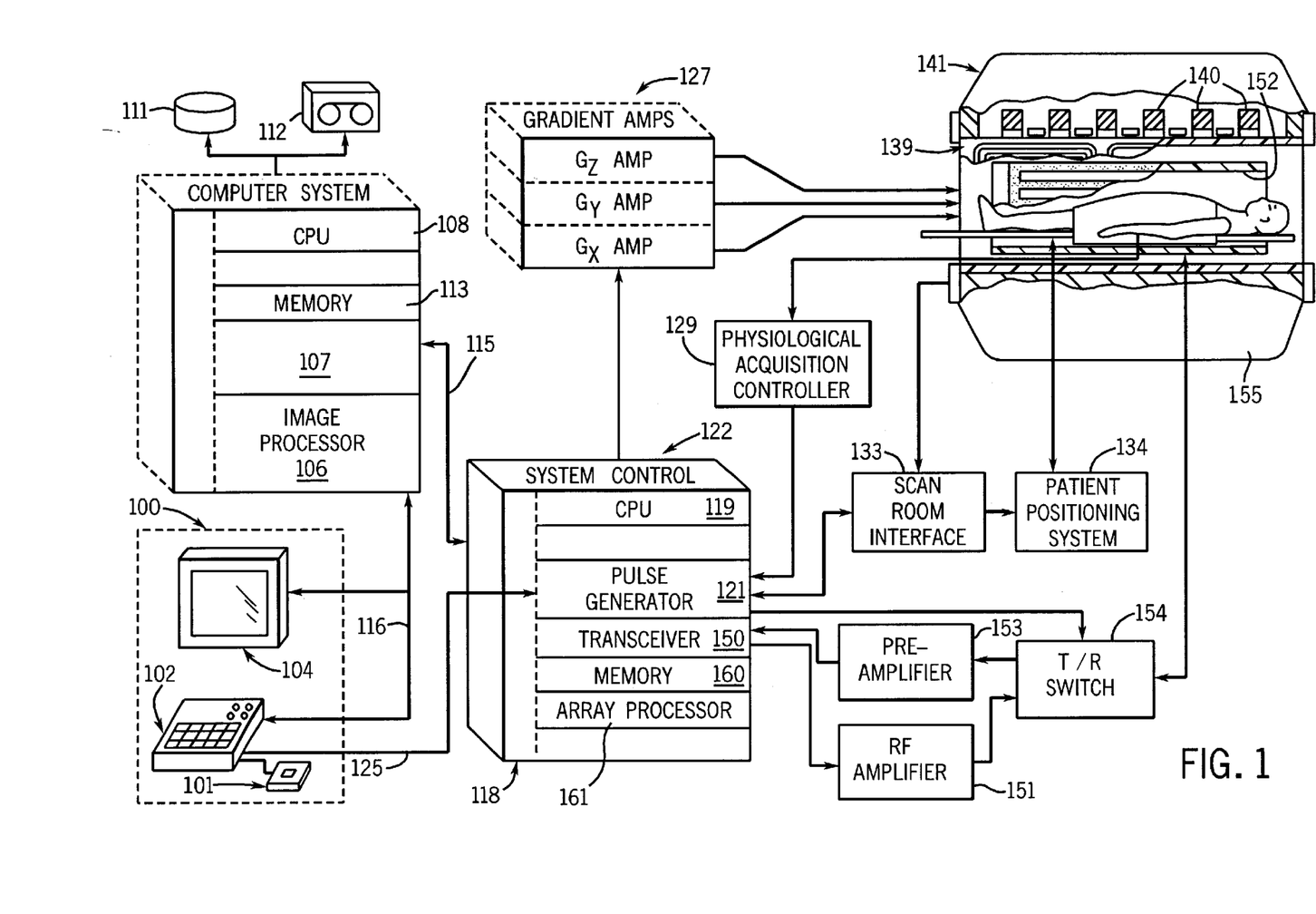
FIG. 1 is a block diagram of an improved MR imaging system.

Referring first to FIG. 1, there is shown the major components of an magnetic resonance (MR) imaging system which represents an embodiment of a method and apparatus for magnetic resonance imaging intersecting slices. The operation of the system is controlled from an operator console 100 which includes an input device 101, a control panel 102 and a display 104. The console 100 communicates through a link 116 with a separate computer system 107 that enables an operator to control the production and display of images on the display 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows, or a structure of interest. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152.

A transceiver module 150 in the system control 122 produces pulses which are amplified by an RF amplifier 151 and coupled to the RF coil 152 by a transmit/receiver switch 154. The resulting signals radiated by the excited nuclei in the patient may be sensed by the RF coil 152 and coupled through the transmit/receive switch 154 to a preamplifier 153. The amplified MR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The MR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
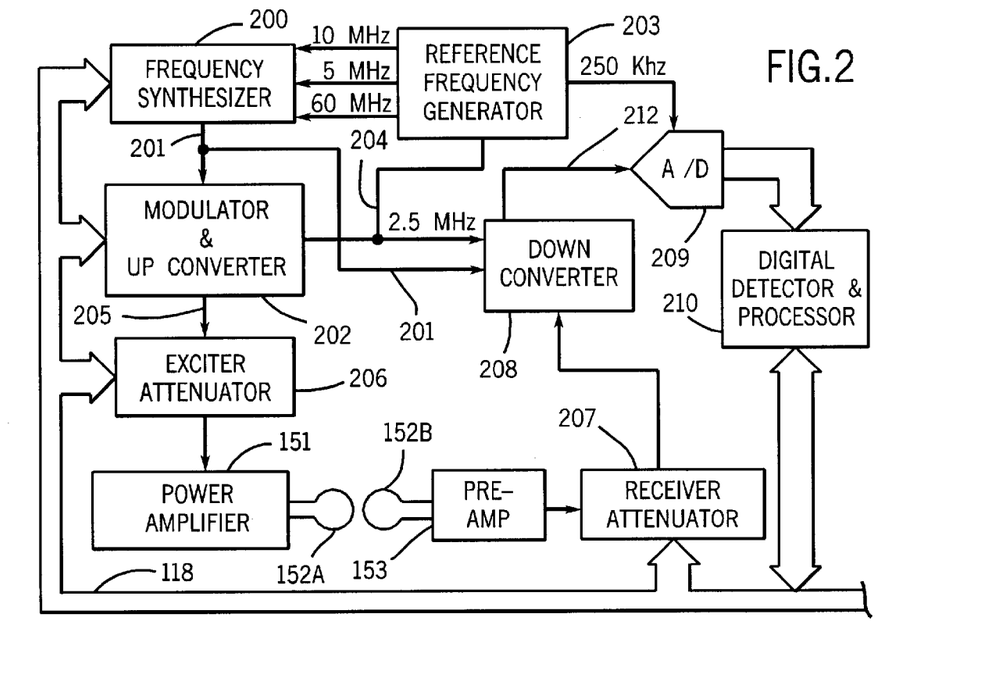
FIG. 2 is an electrical block diagram of the transceiver block which forms part of the MR imaging system of FIG. 1.

Referring particularly to FIGS. 1 and 2, the transceiver 150 produces the RF excitation field $B_1$ through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals (CF) from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the MR signal produced by the subject is picked up by the receiver coil 152B and applied through the preamplifier 153 to the input of a receiver attenuator 207. The receiver attenuator 207 further amplifies the signal by an amount determined by a digital attenuation signal (RA) received from the backplane 118.

The received signal is at or around the Larmor frequency, and this high frequency signal is down converted in a two step process by a down converter 208 which first mixes the MR signal with the carrier signal on line 201 and then mixes the resulting difference signal with the 2.5 MHz reference signal on line 204. The down converted MR signal is applied to the input of an analog-to-digital (A/D) converter 209 which samples and digitizes the analog signal and applies it to a digital detector and signal processor 210 which produces 16 bit in-phase (I) values and 16-bit quadrature (Q) values corresponding to the received signal. The resulting stream of digitized I and Q values of the received signal are output through backplane 118 to the memory module 160 where they are normalized in accordance with the present invention and then employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

In one embodiment of the present invention, an operator can interactively identify and track the movement and/or orientation of a freely moving structure of interest, such as a fetus within a mother's womb, which may possibly have gross bulk movements; or selectively turn off the movement and orientation features when a static or quasi-static structure of interest is present. Such interactive movement and/or orientation identification is accomplished from the operator console 100 (also referred to as an operator interface) using the input device 101. The input device 101 is selected from a group including, but not limited to, a mouse, a joystick, a keyboard, a trackball, a touch screen, a light wand, a voice control, and a platform-mounted spatial manipulation device (such as a Spaceball™ manufactured by Spacetec, Inc. of Lowell, Mass.). The MR imaging system of the preferred embodiment is capable of imaging in any desired orientation within the structure of interest and is equipped to perform both real-time acquisitions and non real-time acquisitions. In particular, real-time refers to continuous acquisition and reconstruction of MR image data as rapidly as it is acquired.

A real-time MR image can be acquired and displayed in approximately one second or less, as constrained by MR imaging system performance.

Figure 3:
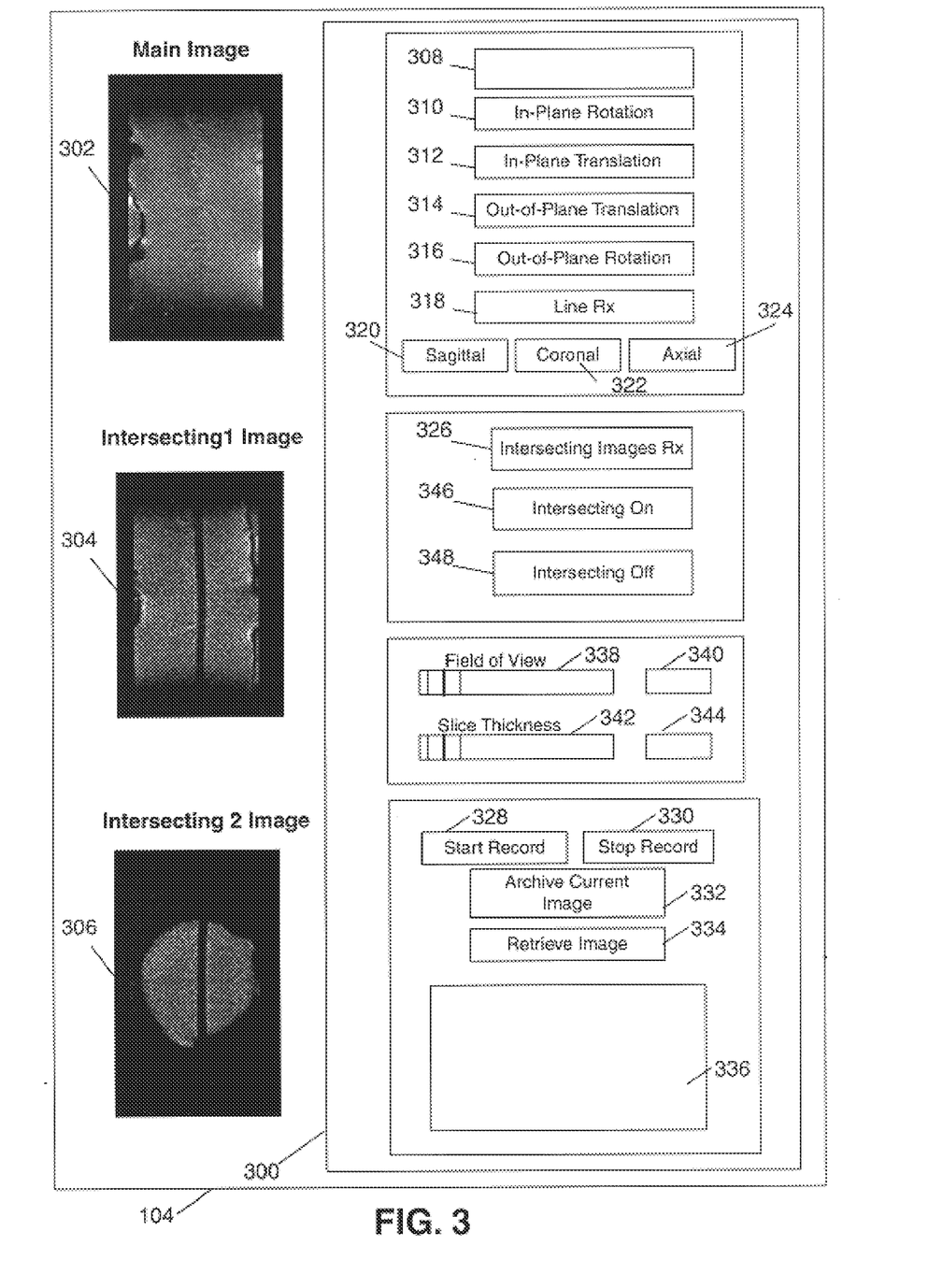
FIG. 3 is an illustration of a graphical user interface on a display screen of an operator console of the MR imaging system of FIG. 1.

FIG. 3 shows the display 104 (also referred to as an electronic display) of the MR imaging system preferably displaying a graphical user interface 300, a main image window 302, a first intersecting image window 304, and a second intersecting image window 306. As described in further detail hereinafter, a main MR image having a main scan or imaging plane through a main slice of interest of the freely moving structure is displayed on the main image window 302. A first intersecting MR image having a first intersecting scan or imaging plane through a first intersecting slice of interest of the freely moving structure is displayed on the first intersecting image window 304. And a second intersecting MR image having a second intersecting scan or imaging plane through a second intersecting slice of interest of the freely moving structure is displayed on the second intersecting image window 306. The operator interacts with the graphical user interface 300 using the input device 101.

First, to effectively utilize the information conveyed by the main image of the freely moving structure of interest in the main viewing window 302, it is desirable for the operator to be able to identify the orientation of the main scan plane so that the operator may appreciate what he or she is viewing. To this end, the preferred embodiment sequentially acquires and displays at least three intersecting images of the freely moving structure so that the operator can identify the main scan plane orientation of the main image relative to such freely moving structure. In detail, the three intersecting images comprise the main image acquired and displayed in the main image window 302, and its two associated intersecting images, i.e., the first and second intersecting images, similarly acquired and displayed in the first and second intersecting image windows 304, 306 respectively. The main, first intersecting, and second intersecting slices, and accordingly each its respective scan planes, are orthogonal to and intersect with each other. Alternatively, the first and second intersecting slices need not be orthogonal to the main slice or to each other. Instead, the first and second intersecting slices may be intersecting radial slices such as slices rotated by 60 and 120 degrees around the same axis from the main slice. This and any other predetermined orientations of the scan planes relative to each other may be equally effective depending on the structure of interest or its movements. Moreover, there may be more than two associated intersecting images for each main image, as desired. Hereinafter the preferred embodiment shall be described with continuing references being made to three intersecting images that are orthogonal to and intersect with each other. However, it should be understood that this shall be done for consistent illustration purposes only and in no way limits the scope of the preferred and alternate embodiments.

The intersection of the main slice with the first intersecting slice is indicated on the first intersecting image displayed on window 304. Intersection of the main slice with the second intersecting slice is indicated on the second intersecting image displayed on window 306. In this manner, by providing images of the freely moving structure from at least three different viewpoints and by knowing the relationship between the scan planes of these three images, the operator can utilize the multiple image views to ascertain the orientation of the main image relative to the structure and safely identify the information contained within the main image.

Second, to identify and track the movement of the freely moving structure, it is desirable for the operator to have a time series of images, preferably sequential sets of the three intersecting images described above, and real-time scan plane prescription methods to selectively modify and fine-tune any or all of each set of the three intersecting images in accordance with the structure's movements. As is apparent, changes, i.e., movement, in the structure of interest can not be detected from any one main image, or even any one main image with its associated two intersecting images. Instead, two or more images having similar scan planes, or more preferably two or more sets of three intersecting images, acquired at consecutive times are necessary to identify movement in the structure imaged therein. Thus, in the preferred embodiment, there is provided continuously updated acquisition, reconstruction, and display of the three intersecting images in real-time.

When performing continuously updated real-time acquisition, reconstruction, and display of the three intersecting images, in order to maintain the maximum possible temporal resolution of the main image (the main image being the MR image intended to be used for actual diagnostic purposes), the acquisition of each main image is interleaved with the acquisition of one of its two intersecting images. In other words, the acquisition of the first intersecting image will be alternated with the acquisition of the second intersecting image, and in between each first and then second intersecting image acquisitions will be the acquisition of the main image. In this way, the temporal resolution of the main image is twice that of each of the first or second intersecting image, and each main image will still have two intersecting images associated therewith, the intersecting image acquired immediately before it and the intersecting image acquired immediately after it. In turn, each intersecting image is associated with two main images, the main image acquired before it and the main image acquired after it. For example, if the main image has sagittal slice orientation and intersecting orthogonal images are desired, then its two intersecting images would have coronal and axial slice orientations, and the interleaving scheme described above would result in the acquisition and display order of the following slice orientations: coronal, sagittal, axial, sagittal, coronal, sagittal, axial, etc.

Interleaved intersecting images, however, can suffer from at least two different distinct artifacts that appear on each of the three intersecting images depending on the relative values of a time of repetition (TR) of the MR imaging pulse sequence and a T1 relaxation constant of the structure. The artifacts can appear when TR is approximately equal to or less than T1 of the structure. In the preferred embodiment, these two artifacts are selectively eliminated or reduced by the use of dephasing gradients and different tip angles. The first artifact eliminated is a very bright, zipper-like artifact resulting from stimulated echos. This bright artifact appears along the intersection of the preceding and current intersecting slices of interest and is eliminated in each image by adding dephasing gradients to the end of each MR imaging pulse sequence corresponding to each of these intersecting images such that stimulated echos in future excitations are avoided.

The second artifact is a dark band similarly resulting from repeated excitation of the same nuclei located in the intersecting region of the preceding and current intersecting slices of interest. Such overlapping excitation of the nuclei in the intersecting region by the preceding and current MR imaging pulse sequences without sufficient relaxation time therebetween results in lower signal in that intersecting region and hence the dark band artifact.

It should be noted, however, that the dark band artifact is only undesirable in the main image because this image is intended for diagnostic purpose. The dark band artifact in the first and second intersecting images, in which each dark band indicates the intersection with the main slice of interest, is desirable because these images are primarily intended for localization and visualization of the main image only. Because these intersecting images are interleaved, the main image is acquired twice as often as each of the first and second intersecting images. For example, if each image requires 125 milliseconds (ms) to acquire, reconstruct, and display, then a new main image is acquired every 250 ms (i.e., the main image is every second acquisition) while a new first intersecting image, or alternatively a new second intersecting image, is acquired every 500 ms (i.e., the first intersecting image is every fourth acquisition). This gives each first and second intersecting slice excitation twice as long for its magnetization to relax before its next excitation in comparison to the main slice excitations. All things being equal, more magnetization relaxation between consecutive excitations results in a higher signal-to-noise (S/N) ratio in the image, and hence in the case of interleaved intersecting images, each first and second intersecting image has a higher S/N ratio then each main image.

So in order to minimize the dark band artifact from the main image while maintaining it in the first and second intersecting images, a first and second intersecting MR imaging pulse sequences corresponding to the first and second intersecting slices of interest, respectively, are configured such that a smaller tip angle excitation will occur in each of the first and second intersecting slices than in the main slice. In fact, in addition to the resulting minimization of the dark band artifact in the main image, the preferred embodiment further provides for approximately the same overall SIN ratio in all three intersecting images. The overall S/N ratios in all the images can be made to be approximately the same even though a first and a second intersecting tip angles of the first and second intersecting slices, respectively, are each lower then a main tip angle of the main slice because in the first and second intersecting images, the reduction in S/N ratio caused by the lower tip angles is compensated for by the increased S/N ratio due to the longer time available for magnetization relaxation between slice excitations. Alternatively, since the main image is the image intended for diagnosis, the first and second intersecting tip angles can be manipulated to result in a lower overall S/N ratio for the first and second intersecting images than the overall S/N ratio for the main image.

Preferably, the main tip angle is two to four times either the first or second intersecting tip angle, wherein all tip angles range between zero to 90 degrees from the vertical. For example, the first and second intersecting tip angles are each at approximately 10 degrees and the main tip angle is at approximately 40 degrees. In another example, the first and second intersecting tip angles are each at approximately 15 degrees and the main tip angle is at approximately 30 degrees.

Shown in FIG. 3 is an illustration of a set of three real-time intersecting images resulting from the tip angles in the former example above. Specifically, all the images were acquired at a TR of 155 ms per slice and the main image displayed in window 302 is a sagittal slice, the first intersecting image displayed in window 304 is a coronal slice, and the second intersecting image displayed in window 306 is an axial slice. The dark band artifacts (usually a horizontal line and a vertical line running along the middle of the main image) in the main image have both been almost entirely eliminated. In contrast, in the first and second intersecting images, the dark band artifact indicating their slice intersection with each other (a horizontal line running along the middle of each of the first and second intersecting images) has been reduced, while the dark band artifact indicating the intersection to the main slice (a vertical line running along the middle of each of the first and second intersecting images) has been preserved.

Next, real-time scan plane prescription is made possible using the display 104, graphical user interface 300, main image window 302, first intersecting image window 304, second intersecting image window 306, and input device 101. In the preferred embodiment, the main slice can be interactively prescribed to any orientation within the entire imaging space in real-time. The first and second intersecting slices can be interactively prescribed in a limited manner, to be described in greater detail hereinafter. Referring to FIG. 3, the graphical user interface 300 includes the following interactive main scan plane prescription tools: an in-plane rotation icon 310, an in-plane translation icon 312, an out-of-plane translation icon 314, an out-of-plane rotation icon 316, a line prescription icon 318, a sagittal icon 320, a coronal icon 322, and an axial icon 324.

Icons 310, 312, 314, 316, 318 allows the operator to select among five different methods of main scan plane prescription, all of which utilize a unique pictorial icon and the input device 101 on the current main image displayed on the main image window 302 to provide real-time interactivity and continuous feedback about the prescription of the next main scan plane in progress. Briefly, the in-plane rotation 310 provides one degree of freedom, permitting the operator to prescribe a new main scan plane that is in the same plane as the current main scan plane but rotated by a certain angle. The in-plane translation icon 312 provides two degrees of freedom, permitting the operator to prescribe the new main scan plane that is in the same plane as the current main scan plane but displaced up/down and/or left/right with respect to the current main scan plane. The out-of-plane translation icon 314 provides one degree of freedom, permitting the operator to "push" or "pull" the current main scan plane into or out of the display 104 to prescribe the new main scan plane. The out-of-plane rotation icon 316 provides two degrees of freedom, permitting the operator to prescribe the new main scan plane that is rotated about a horizontal and/or vertical axis indicated on the current main image. The line prescription icon 318 permits the operator to prescribe a line on any of the current images displayed, including the current first or second intersecting image, along which the next main scan plane will be perpendicular thereto. For a more detailed description of the various scan plane prescription tools, reference is made to U.S. Pat. Nos. 5,512,826 and 5,512,827 which are incorporated herein by reference.

In practice, the operator selects the desired main scan plane prescription tool by "clicking" on one of the icons 310–318 with the input device 101. This selection causes a corresponding pictorial icon, such as a crossbar, a curved arrow, a hand, etc., (not shown in FIG. 3) to be overlaid on the current main image displayed in the main image window 302. The operator then manipulates this pictorial icon on the current main image using input device 101 to prescribe or specify how the current main slice plane should be changed. Once the operator releases input device 101 or alternatively indicates that the prescription has been completed, this prescription information is transmitted via link 125 from the operator console 100 to the system control 122, the prescription information being processed and provided to the pulse generator 121 for the next main image acquisition.

The sagittal, coronal, and axial icons 320, 322, 324 provide an alternate method of prescribing the next main scan plane. Specifically, the MR imaging system provides three pre-defined scan planes having a sagittal orientation, a coronal orientation, and an axial orientation in which they are all intersecting to and intersect (in the middle) with each other. In this manner, these predefined scan plane icons 320, 322, 324 provide the operator with well-known orientations from which to initially image the freely moving structure as well as provide default orientations that the operator can turn to if he should become confused during a series of dynamic prescriptions as provided by icons 310–318.

To prescribe the slice position of the next first and second intersecting scan planes, an intersecting prescription icon 326 is provided on the graphical user interface 300. The operator selects the intersecting prescription icon 326 using input device 101 and a unique pictorial icon (not shown) corresponding to this selection will appear on the current main image in the main image window 302. The prescription is completed by manipulating this pictorial icon to a desired point on the current main image, whereby this selected point specifies an intersection point of the next main, first intersecting, and second intersecting scan planes. Alternatively the unique pictorial icon would not even be needed if the system will accept the intersection point selection directly from the input device 101, such as clicking on a point on the current main image, explicitly specifying the intersection point using geometry coordinates, etc.

Although not shown in FIG. 3, the graphical user interface 300 can further include one or more intersecting prescription icons and image windows such that the operator can define the orientations of the intersecting slices relative to the main slice, including selecting orthogonal intersecting slices, radially intersecting slices, specifying the angle for each radially intersecting slice, the number of intersecting slices, etc. Moreover, the prescription tools on graphical user interface 300 can alternatively be implemented using graphical-type icons (e.g., slide bar icons to rotate or translate) or through explicit prescription (e.g., geometry coordinates).

Upon completion of the next main scan plane prescription using the prescription tools described above, the orientations of the next first and second intersecting scan planes will automatically be updated using the latest first and second intersecting scan plane definitions available and the newly prescribed main scan plane. For example, if the intersecting slices have been defined as intersecting orthogonal slices, then the orientations of the next first and second intersecting scan planes will automatically be updated to the two scan planes that are orthogonal to the newly prescribed main scan plane.

It should be understood that in the preferred embodiment, the MR imaging system will continuously update the three intersecting images in real-time using the latest scan plane prescription available. Thus, if the operator is relatively slow in performing the next scan plane prescription, the main image in which he or she is prescribing can actually be replaced by a more current main image. While this could be irritating from a prescription standpoint, unless the operator is provided with the most current information about the orientation and movement of the freely moving structure, his prescription may be significantly outdated even before it is completed.

To further interactively identify and track the movement and/or orientation of the freely moving structure, the graphical user interface 300 also includes an image label icon 308, a start record icon 328, a stop record icon 330, an archive current image icon 332, a retrieve icon 334, and a log window icon 336. Image label icon 308 contains a unique name specified by the operator, of so inputted, for the images currently being displayed on windows 302, 304, 306. The start and stop record icons 328, 330 allows the operator to continuously "record" all the images displayed and updated on windows 302, 304, 306. The recorded images or more preferably the MR data sets corresponding to the images, are stored in the disk memory 111 or the tape drive 112. Alternatively, the MR imaging system may include additional storage devices to directly store these images in image form rather than in MR data set form (not shown in FIG. 1). Similarly, the archive current image icon 332 allows the operator to record or store one set of images, i.e., the current three intersecting images being displayed. The archive current image icon 332 provides the one-time snapshot feature while the start and stop record icons 328, 330 provides the continuous serial snapshot feature.

When the start record icon 328 or the archive current image icon 332 is selected, each image to be stored will be given a unique identification scheme so that each image can be easily associated with its corresponding intersecting images and be retrieved based on one of several criteria. The unique identification scheme may be an alphanumeric indicia in one or more data fields which is incremented for each image to be stored. For example, the unique identification scheme may be unique slice, frame, and echo numbers. Then the slice number could be incremented every time the start record icon 328 or the archive current image icon 332 is selected, the frame number could be incremented every time the main image is acquired, and the echo number could be pre-defined as "1" for the main image, "2" for the first intersecting image, and "3" for the second intersecting image. Such an image labeling scheme would allow the images to be easily sorted by acquisition order, selectively searched and/or retrieved with or without the interleaved intersecting images, and provide easy association between each main image and its first and second intersecting images.

Moreover, the unique name in the image label icon 308 associated with a given set of images can also be linked with the slice, frame, and echo numbers for those given images when the images are being recorded or stored. In this manner, the retrieve image icon 334 can be selected, which will temporarily stop the continuous real-time acquisition, reconstruction, and display of the three intersecting images, and instead allow the operator to specify the image or images desired to be retrieved, retrieve these images, and then display such images on windows 302, 304, 306. When any of these images are being displayed, if it had a unique name previously specified by the operator, this name will also be displayed on the image label icon 308. The log window icon 336 contains a running list of the unique names give to each image set by their acquisition order, otherwise indicate each set of the three intersecting images which have been displayed in windows 302, 304, 306, and/or indicate which images have been recorded or stored so that the operator can specify which stored image or images are to be retrieved using input device 101.

To still further interactively identify and track the movement and/or orientation of the freely moving structure, a field of view icon 338, a numerical field of view icon 340, a slice thickness icon 342, a numerical slice thickness icon 344, an intersecting off icon 346, and an intersecting on icon 348 are included on graphical user interface 300. In the preferred embodiment, the field of view and slice thickness icons 338, 342 are slide bar icons which can be manipulated with the input device 101 to respectively specify the size of the field of view of all the images (the main, first intersecting, and second intersecting images all having the same field of view) and to specify the slice thickness of all the images (again, the main, first intersecting, and second intersecting images all having the same slice thickness).

Alternatively, the numerical icons 340, 344 will accept an explicit (i.e., number) field of view or slice thickness, respectively. Finally, the intersecting on and off icons 346, 348 permits the operator to selectively stop or resume in real-time the acquisition, reconstruction, and display of both of the next first and second intersecting images. This feature is useful when the operator desires the acquisition of the main slice to be at an even higher temporal resolution. Notice that when the intersecting off icon 348 has been clicked, no images will be displayed on the first and second intersecting image windows 304, 306 and thus, any storage or recordation thereafter will only encompass the main images.

It should be apparent that there has been provided in accordance with one embodiment of the present invention a method for accurately and efficiently identifying and tracking the movement and orientation of a freely moving structure of interest using interleaved intersecting MR images. While the embodiments illustrated in the FIGs. and described above are presently preferred, it should be understood that these embodiments are offered by way of example only. For example, the MR imaging system described herein may be an open body MR imaging system. Still further, the electronic display of the system may simultaneously display multiple sets of three intersecting images, so that for example, the operator can simultaneously view the most current set of three intersecting images as well as previously recorded images. Furthermore, it is contemplated that the invention may be applied to systems other than medical systems which can benefit from orientation and/or movement information of an unpredictably moving structure of interest. Accordingly, the invention is not limited to a particular embodiment, but extends to alternatives, modifications, and variations that nevertheless fall within the spirit and scope of the appended claims.

What is claimed is:

1. A method for viewing a structure of interest positioned in a magnetic resonance (MR) imaging system, comprising:
   (a) generating a main MR image having a main scan plane through a main slice of the structure of interest;
   (b) configuring a main MR imaging pulse sequence of the main MR image to cause a main tip angle in the main slice;
   (c) displaying the main MR image;
   (d) generating a first intersecting MR image having a first intersecting scan plane through a first intersecting slice of the structure of interest, wherein the first intersecting scan plane intersects with the main scan plane;
   (e) configuring a first intersecting MR imaging pulse sequence of the first intersecting MR image to cause a first intersecting tip angle in the first intersecting slice;
   (f) displaying the first intersecting MR image;
   (g) generating a second intersecting MR image having a second intersecting scan plane through a second intersecting slice of the structure of interest, wherein the second intersecting scan plane intersects with the main and first intersecting scan planes;
   (h) configuring a second intersecting MR imaging pulse sequence of the second intersecting MR image to cause a second intersecting tip angle in the second intersecting slice; and
   (i) displaying the second intersecting MR image, wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

2. The method of claim 1, wherein the displaying steps (c), (f), and (i) include simultaneously displaying the main, first intersecting, and second intersecting MR images to permit identification of the orientation of the main slice.

3. The method of claim 1, wherein at least one of the first and second intersecting MR image includes an indication of an intersecting region between the corresponding at least one of the first and second intersecting slice with the main slice when at least one of the first and second intersecting tip angle is smaller than the main tip angle.

4. The method of claim 3, wherein the main tip angle is 2 to 4 times at least one of the first and second intersecting tip angle.

5. The method of claim 4, wherein at least one of the first and second intersecting tip angle is approximately 10 degrees and the main tip angle is approximately 40 degrees.

6. The method of claim 4, wherein at least one of the first and second intersecting tip angle is approximately 15 degrees and the main tip angle is approximately 30 degrees.

7. The method of claim 1, wherein at least one of the main, first intersecting, and second intersecting MR imaging pulse sequence includes a dephasing gradient at the end thereof.

8. The method of claim 1, further comprising repeating steps (a) to (i) a plurality of times as desired in continuous real-time, wherein the generating step (d) for the first intersecting MR image, the generating step (g) for the second intersecting MR image, and the generating step (a) for the main MR image are interleaved.

9. The method of claim 8, further comprising prescribing the subsequent orientation of at least one of the main, first intersecting, and second intersecting scan plane.

10. The method of claim 8, further comprising:
    storing at least one of the main, first intersecting, and second intersecting MR image in the MR imaging system, wherein each MR image stored is associated with an identification scheme; and
    retrieving at least one of the main, first intersecting, and second intersecting MR image stored in the MR imaging system, wherein the identification scheme permits selective retrieval of the desired MR image.

11. The method of claim 1, wherein the main, first intersecting, and second intersecting scan planes have orientations selected from a group including an intersecting orthogonal orientation, an intersecting radial orientation, and an any other pre-determined orientation, as desired.

12. A system for viewing a structure of interest positioned therein, comprising:
    (a) means for generating a main MR image having a main scan plane through a main slice of the structure of interest;
    (b) means for configuring a main MR imaging pulse sequence of the main MR image to cause a main tip angle in the main slice;
    (c) means for displaying the main MR image;
    (d) means for generating a first intersecting MR image having a first intersecting scan plane through a first intersecting slice of the structure of interest, wherein the first intersecting scan plane intersects with the main scan plane;

(e) means for configuring a first intersecting MR imaging pulse sequence of the first intersecting MR image to cause a first intersecting tip angle in the first intersecting slice;

(f) means for displaying the first intersecting MR image;

(g) means for generating a second intersecting MR image having a second intersecting scan plane through a second intersecting slice of the structure of interest, wherein the second intersecting scan plane intersects with the main and first intersecting scan planes;

(h) means for configuring a second intersecting MR imaging pulse sequence of the second intersecting MR image to cause a second intersecting tip angle in the second intersecting slice; and (i) means for displaying the second intersecting MR image, wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

13. The system of claim 12, wherein the means for displaying (c), (f), and (i) include simultaneous display of the main, first intersecting, and second intersecting MR images to permit identification of the orientation of the main slice.

14. The system of claim 12, wherein at least one of the first and second intersecting MR image includes an indication of an intersecting region between the at least one of the first and second intersecting slice with the main slice when at least one of the first and second intersecting tip angle is smaller than the main tip angle.

15. The system of claim 14, wherein the main tip angle is 2 to 4 times at least one of the first and second intersecting tip angle.

16. The system of claim 15, wherein at least one of the first and second intersecting tip angle is approximately 10 degrees and the main tip angle is approximately 40 degrees.

17. The system of claim 15, wherein at least one of the first and second intersecting tip angle is approximately 15 degrees and the main tip angle is approximately 30 degrees.

18. The system of claim 12, wherein at least one of the main, first intersecting, and second intersecting MR imaging pulse sequence includes a dephasing gradient at the end thereof.

19. The system of claim 12, wherein each of the main, first intersecting, and second intersecting MR images can be updated repeatedly in continuous real-time as desired, the generation of each of the first and second intersecting MR image alternating and thereinbetween, interleaved with the generation of the main MR image.

20. The system of claim 19, further comprising means for prescribing the subsequent orientation of at least one of the main, first intersecting, and second intersecting scan plane.

21. The system of claim 19, further comprising:

means for storing at least one of the main, first intersecting, and second intersecting MR image in the system, wherein each MR image stored is associated with an identification scheme; and means for retrieving and displaying at least one of the main, first intersecting, and second intersecting MR image stored in the system, wherein the identification scheme permits selective retrieval of the desired MR image.

22. The system of claim 12, wherein the main, first intersecting, and second intersecting scan planes have orientations selected from a group including an intersecting orthogonal orientation, an intersecting radial orientation, and an any other pre-determined orientation, as desired.

23. A magnetic resonance (MR) imaging system for viewing a structure of interest positioned therein, comprising:

a MR imaging device configured to generate a main MR image having a main scan plane through a main slice of the structure of interest, a first intersecting MR image having a first intersecting scan plane through a first intersecting slice of the structure of interest, and a second intersecting MR image having a second intersecting scan plane through a second intersecting slice of the structure of interest, and configured to cause a main MR imaging pulse sequence of the main MR image to generate a main tip angle in the main slice, a first intersecting MR imaging pulse sequence of the first intersecting MR image to generate a first intersecting tip angle in the first intersecting slice, and a second intersecting MR imaging pulse sequence of the second intersecting MR image to generate a second intersecting tip angle in the second intersecting slice, wherein the main, first intersecting, and second intersecting scan planes intersect with each other; and an operator interface coupled to the MR imaging device, configured to receive the generated main, first intersecting, and second intersecting MR images therefrom and to display the main, first intersecting, and second intersecting MR images, wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

24. The system of claim 23, wherein the operator interface includes an electronic display and the operator interface simultaneously displays the main, first intersecting, and second intersecting MR images to permit identification of the orientation of the main slice.

25. The system of claim 23, wherein at least one of the first and second intersecting MR image includes an indication of an intersecting region between the corresponding at least one of the first and second intersecting slice with the main slice when at least one of the first and second intersecting tip angle is smaller than the main tip angle.

26. The system of claim 25, wherein the main tip angle is 2 to 4 times at least one of the first and second intersecting tip angle.

27. The system of claim 26, wherein at least one of the first and second intersecting tip angle is approximately 10 degrees and the main tip angle is approximately 40 degrees.

28. The system of claim 26, wherein at least one of the first and second intersecting tip angle is approximately 15 degrees and the main tip angle is approximately 30 degrees.

29. The system of claim 23, wherein at least one of the main, first intersecting, and second intersecting MR imaging pulse sequence includes a dephasing gradient at the end thereof.

30. The system of claim 23, wherein the MR imaging device continuously updates each of the main, first intersecting, and second intersecting MR images in real-time as desired and the operator interface correspondingly displays each updated MR image, the generation of each of the first and second intersecting MR image alternating and thereinbetween, interleaved with the generation of the main MR image.

31. The system of claim 30, wherein the operator interface is configured to transmit a prescription signal in response to an operator prescribing the subsequent orientation of at least one of the main, first intersecting, and second intersecting scan plane.

32. The system of claim 30, further comprising a storage device coupled to the MR imaging device and configured to store at least one of the main, first intersecting, and second intersecting MR image, and an identification scheme associated with each MR image, in response to a store signal received from the operator interface, and wherein the operator interface is configured to transmit a retrieval signal in response to an image retrieval selection made on the operator interface to selectively retrieve at least one of the main, first intersecting, and second intersecting MR image stored in the storage device.

33. The system of claim 30, wherein the operator interface includes an input device selected from a group including a mouse, a joystick, a keyboard, a trackball, a touch screen, a light wand, a voice control, and a platform-mounted spatial manipulation device.

34. The system of claim 23, wherein the main, first intersecting, and second intersecting scan planes have orientations selected from a group including an intersecting orthogonal orientation, an intersecting radial orientation, and an any other pre-determined orientation, as desired.

35. A method for viewing a structure of interest positioned in a magnetic resonance (MR) imaging system, comprising:
   (a) generating a main MR image having a main scan plane through a main slice of the structure of interest;
   (b) displaying the main MR image;
   (c) generating a first intersecting MR image having a first intersecting scan plane through a first intersecting slice of the structure of interest, wherein the first intersecting scan plane intersects with the main scan plane;
   (d) displaying the first intersecting MR image;
   (e) generating a second intersecting MR image having a second intersecting scan plane through a second intersecting slice of the structure of interest, wherein the second intersecting scan plane intersects with the main and first intersecting scan planes;
   (f) displaying the second intersecting MR image; and
   (g) repeating steps (a) to (f) a plurality of times as desired in continuous real-time, wherein the generating steps (c) and (e), respectively, of the first and second intersecting MR image alternates and thereinbetween, interleaved with the generating step (a) of each of the main MR image.

36. The method of claim 35, wherein the displaying steps (b), (d), and (f) include simultaneously displaying the main, first intersecting, and second intersecting MR images to permit identification of the orientation of the main slice.

37. The method of claim 35, further comprising:
   configuring a main MR imaging pulse sequence of the main MR image to cause a main tip angle in the main slice;
   configuring a first intersecting MR imaging pulse sequence of the first intersecting MR image to cause a first intersecting tip angle in the first intersecting slice; and
   configuring a second intersecting MR imaging pulse sequence of the second intersecting MR image to cause a second intersecting tip angle in the second intersecting slice,
   wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

38. The method of claim 37, wherein the main tip angle is 2 to 4 times at least one of the first and second intersecting tip angle.

39. The method of claim 37, wherein at least one of the main, first intersecting, and second intersecting MR imaging pulse sequence includes a dephasing gradient at the end thereof.

40. The method of claim 35, further comprising prescribing the subsequent orientation of at least one of the main, first intersecting, and second intersecting scan plane.

41. The method of claim 35, further comprising:
   storing at least one of the main, first intersecting, and second intersecting MR image in the MR imaging system, wherein each MR image stored is associated with an identification scheme; and
   retrieving and displaying at least one of the main, first intersecting, and second intersecting MR image stored in the MR imaging system, wherein the identification scheme permits selective retrieval of the desired MR image.

42. The method of claim 35, wherein the main, first intersecting, and second intersecting scan planes have orientations selected from a group including an intersecting orthogonal orientation, an intersecting radial orientation, and an any other pre-determined orientation, as desired.

43. A magnetic resonance (MR) imaging system for viewing a structure of interest positioned therein, comprising:
   (a) means for generating a main MR image having a main scan plane through a main slice of the structure of interest;
   (b) means for displaying the main MR image;
   (c) means for generating a first intersecting MR image having a first intersecting scan plane through a first intersecting slice of the structure of interest, wherein the first intersecting scan plane intersects with the main scan plane;
   (d) means for displaying the first intersecting MR image;
   (e) means for generating a second intersecting MR image having a second intersecting scan plane through a second intersecting slice of the structure of interest, wherein the second intersecting scan plane intersects with the main and first intersecting scan planes;
   (f) means for displaying the second intersecting MR image; and
   (g) means for repeating steps (a) to (f) a plurality of times as desired in continuous real-time, wherein the generation of each of the first and second intersecting MR image alternates and thereinbetween interleaved with the generation of each of the main MR image.

44. The system of claim 43, wherein the means for displaying (b), (d), and (f) is configured to simultaneously display the main, first intersecting, and second intersecting MR images to permit identification of the orientation of the main slice.

45. The system of claim 43, further comprising:
   means for configuring a main MR imaging pulse sequence of the main MR image to cause a main tip angle in the main slice;

means for configuring a first intersecting MR imaging pulse sequence of the first intersecting MR image to cause a first intersecting tip angle in the first intersecting slice; and means for configuring a second intersecting MR imaging pulse sequence of the second intersecting MR image to cause a second intersecting tip angle in the second intersecting slice, wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

46. The system of claim 45, wherein the main tip angle is 2 to 4 times at least one of the first and second intersecting tip angle.

47. The system of claim 45, wherein at least one of the main, first intersecting, and second intersecting MR imaging pulse sequence includes a dephasing gradient at the end thereof.

48. The system of claim 43, further comprising means for prescribing the subsequent orientation of at least one of the main, first intersecting, and second intersecting scan plane.

49. The system of claim 43, further comprising:
means for storing at least one of the main, first intersecting, and second intersecting MR image in the MR imaging system, wherein each MR image stored is associated with an identification scheme; and
means for retrieving and displaying at least one of the main, first intersecting, and second intersecting MR image stored in the MR imaging system,
wherein the identification scheme permits selective retrieval of the desired MR image.

50. The system of claim 43, wherein the main, first intersecting, and second intersecting scan planes have orientations selected from a group including an intersecting orthogonal orientation, an intersecting radial orientation, and an any other pre-determined orientation, as desired.

51. A magnetic resonance (MR) imaging system for viewing a structure of interest positioned therein, comprising:
a MR imaging device configured to generate a main MR image having a main scan plane through a main slice of the structure of interest, a first intersecting MR image having a first intersecting scan plane through a first intersecting slice of the structure of interest, and a second intersecting MR image having a second intersecting scan plane through a second intersecting slice of the structure of interest; and
an operator interface coupled to the MR imaging device, configured to receive the generated main, first intersecting, and second intersecting MR images therefrom and to display the main, first intersecting, and second intersecting MR images,
wherein the main, first intersecting, and second intersecting MR images are updated continuously in real-time as desired, and wherein the generation of each of the first and second intersecting MR image alternates and thereinbetween interleaved with the generation of each of the main MR image.

52. The system of claim 51, wherein the operator interface includes an electronic display and includes simultaneous display of the main, first intersecting, and second intersecting MR images to permit identification of the orientation of the main slice.

53. The system of claim 51, wherein the MR imaging device is configured to generate a main MR imaging pulse sequence of the main MR image to cause a main tip angle in the main slice, a first intersecting MR imaging pulse sequence of the first intersecting MR image to cause a first intersecting tip angle in the first intersecting slice, and a second intersecting MR imaging pulse sequence of the second intersecting MR image to cause a second intersecting tip angle in the second intersecting slice, wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an an desirable artifact.

54. The system of claim 53, wherein the main tip angle is 2 to 4 times at least one of the first and second intersecting tip angle.

55. The system of claim 53, wherein at least one of the main, first intersecting, arid second intersecting MR imaging pulse sequence includes a dephasing gradient at the end thereof.

56. The system of claim 51, wherein the operator interface is configured to transmit a prescription signal in response to an operator prescribing the subsequent orientation of at least one of the main, first intersecting, and second intersecting scan plane.

57. The system of claim 51, further comprising a storage device coupled to the MR imaging device and configured to store at least one of the main, first intersecting, and second intersecting MR image and an identification scheme associated with each MR image, in response to a store signal received from the operator interface, and wherein the operator interface is configured to transmit a retrieval signal in response to an image retrieval selection made on the operator interface to selectively retrieve at least one of the main, first intersecting, and second intersecting MR image stored in the storage device.

58. The system of claim 51, wherein the main, first intersecting, and second intersecting scan planes have orientations selected from a group including an intersecting orthogonal orientation, an intersecting radial orientation, and an any other pre-determined orientation.

59. A method for viewing a structure of interest positioned in a magnetic resonance (MR) imaging system, comprising:
(a) generating a main MR image having a main scan plane through a main slice of the structure of interest;
(b) displaying the main MR image;
(c) generating a first intersecting MR image having a first intersecting scan plane through a first intersecting slice of the structure of interest, wherein the first intersecting scan plane intersects with the main scan plane;
(d) displaying the first intersecting MR image;
(e) generating a second intersecting MR image having a second intersecting scan plane through a second intersecting slice of the structure of interest, wherein the second intersecting scan plane intersects with the main and first intersecting scan planes;
(f) displaying the second intersecting MR image;
(g) selectively storing at least one of the main, first intersecting, and second intersecting MR image, its associated unique identification scheme, and optionally its unique image name label; and
(h) selectively retrieving at least one of the main, first intersecting, and second intersecting MR image stored based on at least one criterion of the unique identification scheme.

60. The method of claim 59, wherein the unique identification scheme includes an alphanumeric indicia in at least one data field.

61. The method of claim 60, wherein the unique identification scheme includes at least one of a frame counter, a slice counter, and an echo counter, the at least one of the frame, slice, and echo counter being incremented for each MR image being stored.

62. The method of claim 59, further comprising:
configuring a main MR imaging pulse sequence of the main MR image to cause a main tip angle in the main slice;
configuring a first intersecting MR imaging pulse sequence of the first intersecting MR image to cause a first intersecting tip angle in the first intersecting slice; and
configuring a second intersecting MR imaging pulse sequence of the second intersecting MR image to cause a second intersecting tip angle in the second intersecting slice,
wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

63. The method of claim 62, wherein the main tip angle is 2 to 4 times at least one of the first and second intersecting tip angle.

64. The method of claim 59, further comprising prescribing the subsequent orientation of at least one of the main, first intersecting, and second intersecting scan plane.

65. The method of claim 64, wherein the prescribing step includes prescribing the main scan plane to any orientation within an imaging space of the MR imaging system.

66. The method of claim 64, wherein the prescribing step includes prescribing an intersection point on the main MR image, the intersection point defining the intersecting point of the subsequent main, first intersecting, and second intersecting scan planes.

67. The method of claim 64, wherein the prescribing step includes selecting from a group including prescribing an in-plane rotation of the subsequent main slice, an in-plane translation of the subsequent main slice, an out-of-plane translation of the subsequent main slice, an out-of-plane rotation of the subsequent main slice, a perpendicular plane prescription of the subsequent main slice, a sagittal plane prescription of the subsequent main slice, a coronal plane prescription of the subsequent main slice, an axial plane prescription of the subsequent main slice, and an intersecting intersection point prescription of the subsequent first and second intersecting slices.

68. The method of claim 59, further comprising prescribing a field of view and a slice thickness of at least one of the main, first intersecting, and second intersecting MR image.

69. The method of claim 59, wherein the main, first intersecting, and second intersecting scan planes have orientations selected from a group including an intersecting orthogonal orientation, an intersecting radial orientation, and an any other orientation, as desired.

70. The method of claim 59, further comprising repeating steps (a) to (f) a plurality of time continuously in real-time, wherein the generating step (c) for the first intersecting MR image alternates with the generating step (e) for the second intersecting MR image, and the generating step (a) for the main MR image occurs after each of the generating steps (c) and (e).

71. The system of claim 59, wherein the means for displaying (b), (d), and (f) is configured to simultaneous display the main, first intersecting, and second intersecting MR images to permit identification of the orientation of the main slice.

72. A graphical user interface for viewing a structure of interest positioned in a magnetic resonance (MR) imaging system, comprising:
a means for displaying a main MR image of the structure of interest;
a means for displaying a first intersecting MR image of the structure of interest;
a means for displaying a second intersecting MR image of the structure of interest;
a means for selectively storing at least one of the main, first intersecting, and second intersecting MR image, its associated unique identification scheme, and optionally a unique image name label in the MR imaging system; and
a means for selectively retrieving at least one of the main, first intersecting, and second intersecting MR image stored in the MR imaging system based on at least one criterion of the unique identification scheme.

73. The graphical user interface of claim 72, wherein the unique identification scheme includes an alphanumeric indicia in at least one data field.

74. The graphical user interface of claim 73, wherein the unique identification scheme includes at least one of a frame counter, a slice counter, and an echo counter, the at least one of the frame, slice, and echo counter being incremented for each MR image being stored.

75. The graphical user interface of claim 72, further comprising:
a means for configuring a main MR imaging pulse sequence of the main MR image to cause a main tip angle in the main slice;
a means for configuring a first intersecting MR imaging pulse sequence of the first intersecting MR image to cause a first intersecting tip angle in the first interesting slice; and
a means for configuring a second intersecting MR imaging pulse sequence of the second intersecting MR image to cause a second intersecting tip angle in the second intersecting slice,
wherein at least one of the first and second intersecting tip angle is smaller than main tip angle in response to relative values of a time of repetition (TR) of at least one of the main, first intersecting, and second intersecting MR imaging pulse sequence and a T1 relaxation constant of the structure of interest, to minimize an undesirable artifact.

76. The graphical user interface of claim 75, wherein the main tip angle is 2 to 4 times at least one of the first and second intersecting tip angle.

77. The graphical user interface of claim 72, further comprising a means for prescribing the subsequent orientation of at least one of the main, first intersecting, and second intersecting scan plane.

78. The graphical user interface of claim 77, wherein at least one of the means for displaying, the means for prescribing, the means for selectively storing, and the means for selectively retrieving are initiated by an input device selected from a group including a mouse, a joystick, a keyboard, a trackball, a touch screen, a light wand, voice control, and a platform-mounted spatial manipulation device.

79. The graphical user interface of claim 77, wherein the means for prescribing is configured to prescribe the main scan plane to any orientation within an imaging space of the MR imaging system.

80. The graphical user interface of claim 77, wherein the means for prescribing is configured to prescribe an intersection point on the main MR image, the intersection point defining the intersecting point of the subsequent main, first intersecting, and second intersecting scan planes.

81. The graphical user interface of claim 77, wherein the means for prescribing includes selecting from a group including prescribing an in-plane rotation of the subsequent main slice, an in-plane translation of the subsequent main slice, an out-of-plane translation of the subsequent main slice, an out-of-plane rotation of the subsequent main slice, a perpendicular plane prescription of the subsequent main slice, a sagittal plane prescription of the subsequent main slice, a coronal plane prescription of the subsequent main slice, an axial plane prescription of the subsequent main slice, and an intersecting intersection point prescription of the subsequent first and second intersecting slices.

82. The graphical user interface of claim 72, further comprising a means for prescribing a field of view and a slice thickness of at least one of the main, first intersecting, and second intersecting MR image.

83. The graphical user interface of claim 72, wherein the main, first intersecting, and second intersecting scan planes have orientations selected from a group including an intersecting orthogonal orientation, an intersecting radial orientation, and an any other pre-determined orientation.

84. The graphical user interface of claim 72, wherein each of the main, first intersecting, and second intersecting MR images can be updated repeatedly in continuous real-time as desired, and wherein each of the main, first intersecting, and second intersecting MR image is acquired interleaved.

85. The graphical user interface of claim 84, further comprising a means for halting and resuming the acquisition and display of the first and second intersecting MR images as desired.

86. A magnetic resonance (MR) imaging system for viewing a structure of interest positioned therein, comprising:
 a MR imaging device configured to generate a main MR image having a main scan plane through a main slice of the structure of interest, a first intersecting MR image having a first intersecting scan plane through a first intersecting slice of the structure of interest, and a second intersecting MR image having a second intersecting scan plane through a second intersecting slice of the structure of interest, wherein the main, first intersecting, and second intersecting scan planes intersect with each other;
 an operator interface coupled to the MR imaging device, configured to receive the generated main, first intersecting, and second intersecting MR images from the MR imaging device and to display the main, first intersecting, and second intersecting MR images; and
 a storage device coupled to the MR imaging device, configured to selectively store at least one of the main, first intersecting, and second intersecting MR image, it associated unique identification scheme, and optionally a unique image name label, and configured to selectively retrieve at least one of the main, first intersecting, and second intersecting MR image stored in the storage device, the retrieval base on at least one criterion of the unique identification scheme.

87. The system of claim 86, wherein the unique identification scheme includes an alphanumeric indicia in at least one data field of the storage device.

88. The system of claim 87, wherein the unique identification scheme includes at least one of a frame counter, a slice counter, and an echo counter, the at least one of the frame, slice, and echo counter being incremented for each MR image being stored.

89. The system of claim 86, wherein the MR imaging device is configured to generate a main MR imaging pulse sequence of the main MR image to cause a main tip angle in the main slice, a first intersecting MR imaging pulse sequence of the first intersecting MR image to cause a first intersecting tip angle in the first intersecting slice, and a second intersecting MR imaging pulse sequence of the second intersecting MR image to cause a second intersecting tip angle in the second intersecting slice,
 wherein at least one of the first and second intersecting tip angle is smaller than the main tip angle in response to relative values of a time of repetition (TR) of at least one of the main, first intersecting, and second intersecting MR imaging pulse sequence and a T1 relaxation constant of the structure of interest, to minimize an undesirable artifact.

90. The system of claim 89, wherein the main tip angle is 2 to 4 times at least one of the first and second intersecting tip angle.

91. The system of claim 86, wherein the operator interface is configured to transmit a prescription signal in response to an operator prescribing the subsequent orientation of at least one of the main, first intersecting, and second intersecting scan plane.

92. The system of claim 91, wherein the prescription signal transmitted is in response to the operator prescribing the main scan plane to any orientation within an imaging space of the MR imaging system.

93. The system of claim 91, wherein the prescription signal transmitted is in response to the operator prescribing an intersection point on the main MR image, the intersection point defining the intersecting point of the subsequent main, first intersecting, and second intersecting scan planes.

94. The system of claim 91, wherein the prescription signal transmitted is in response to the operator prescribing an in-plane rotation of the subsequent main slice, an in-plane translation of the subsequent main slice, an out-of-plane translation of the subsequent main slice, an out-of-plane rotation of the subsequent main slice, a perpendicular plane prescription of the subsequent main slice, a sagittal plane prescription of the subsequent main slice, a coronal plane prescription of the subsequent main slice, an axial plane prescription of the subsequent main slice, and an intersecting intersection point prescription of the subsequent first and second intersecting slices.

95. The system of claim 86, wherein the operator interface is configured to transmit a prescription signal in response to an operator prescribing a field of view and a slice thickness of at least one of the main, first intersecting, and second intersecting MR image.

96. The system of claim 86, wherein the main, first intersecting, and second intersecting scan planes have orientations selected from a group including an intersecting orthogonal orientation, an intersecting radial orientation, and an any other pre-determined orientation.

97. The system of claim 86, wherein the MR imaging device is configured to update the main, first intersecting, and second intersecting MR images in continuous real-time as desired, the generation of the main, first intersecting, and second intersecting MR images being interleaved, and wherein the operator interface is configured to simultaneously display the main, first intersecting, and second intersecting MR images to permit identification of the orientation of the main slice.

98. The system of claim 86, wherein the operator interface includes an input device selected from a group including a mouse, a joystick, a keyboard, a trackball, a touch screen, a light wand, a voice control, and a platform-mounted spatial manipulation device.

* * * * *

UNITED STATES PATENT AND TRADEMARK OFFICE
CERTIFICATE OF CORRECTION

PATENT NO.    : 6,301,497 B1
DATED         : October 9, 2001
INVENTOR(S)   : David Maier Neustadter It is certified that error appears in the above-identified patent and that said Letters Patent is hereby corrected as shown below:

Column 3,
Line 17, replace "tot he" with -- to the --.

Column 4,
Line 9, replace "anther" with -- another --.

Column 9,
Line 33, replace "SIN" with -- S/N --.

Column 11,
Line 5, replace "predefined" with -- pre-defined --.

Column 14,
Line 53, delete "an".

Column 16,
Line 5, delete "an".

Column 17,
Line 29, delete "an".

Column 18,
Line 32, delete "an".

Column 19,
Line 40, delete "an".

Column 20,
Line 16, replace "an desirable" with -- undesirable --.
Line 21, replace "arid" with -- and --.
Line 44, delete "an".

Column 21,
Line 63, delete "an".

UNITED STATES PATENT AND TRADEMARK OFFICE
CERTIFICATE OF CORRECTION

PATENT NO. : 6,301,497 B1
DATED : October 9, 2001
INVENTOR(S) : David Maier Neustadter It is certified that error appears in the above-identified patent and that said Letters Patent is hereby corrected as shown below:

Column 22,
Line 50, after "than", insert -- the --.

Column 23,
Line 1, after "wand,", insert -- a --.

Signed and Sealed this

Eighth Day of July, 2003

JAMES E. ROGAN
*Director of the United States Patent and Trademark Office*